(12) United States Patent
Fung et al.

(10) Patent No.: US 10,363,111 B2
(45) Date of Patent: Jul. 30, 2019

(54) PHACOEMULSIFICATION SURGICAL MULTI-USE PACK USAGE TRACKER SYSTEM

(71) Applicant: ABBOTT MEDICAL OPTICS INC., Santa Ana, CA (US)

(72) Inventors: Edith W. Fung, Diamond Bar, CA (US); Deep Mehta, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 56 days.

(21) Appl. No.: 15/017,501

(22) Filed: Feb. 5, 2016

(65) Prior Publication Data
US 2017/0224429 A1 Aug. 10, 2017

(51) Int. Cl.
*A61B 50/30* (2016.01)
*A61B 90/00* (2016.01)
*A61F 9/007* (2006.01)
*G08B 21/18* (2006.01)
*A61M 1/00* (2006.01)
(Continued)

(52) U.S. Cl.
CPC .............. *A61B 50/30* (2016.02); *A61B 90/08* (2016.02); *A61F 9/007* (2013.01); *A61M 1/0058* (2013.01); *G08B 21/182* (2013.01); *A61B 90/96* (2016.02); *A61B 90/98* (2016.02); *A61B 2090/0803* (2016.02); *A61B 2090/0814* (2016.02); *A61B 2560/028* (2013.01); *A61F 9/00736* (2013.01); *A61M 2205/12* (2013.01); *A61M 2205/273* (2013.01); *A61M 2210/0612* (2013.01)

(58) Field of Classification Search
CPC ... A61F 9/007; A61F 9/00736; A61M 1/0058; A61M 2205/12; A61M 2205/273; A61M 2210/0612; G08B 21/182; A61B 50/30; A61B 90/08; A61B 2090/0803; A61B 2560/028
See application file for complete search history.

(56) References Cited

U.S. PATENT DOCUMENTS

| 5,396,376 | A | * | 3/1995 | Chambors | G11B 5/584 360/48 |
| 6,036,458 | A | | 3/2000 | Cole et al. | |
| 8,491,528 | B2 | | 7/2013 | Muri et al. | |

(Continued)

OTHER PUBLICATIONS

International Search Report and Written Opinion for Application No. PCT/US2017/016504, dated May 16, 2017, 13 pages.

*Primary Examiner* — James J Yang
(74) *Attorney, Agent, or Firm* — Johnson & Johnson Surgical Vision, Inc.

(57) ABSTRACT

A surgical cassette/pack usage tracker for tracking a number of uses for a cassette/pack to prohibit uses from exceeding a maximum amount. A usage tracker system engages with or scans a portion of the cassette/pack to determine the number of uses. In illustrative embodiments, an implement interacts with a film in the cassette after each use and determines remaining uses for the cassette/pack. In other embodiments, an implement interacts with a rotatable wheel that rotates with each use, the implement configured to permit the tracker to identify the number uses and determine remaining uses for the cassette/pack. When a maximum usage amount is reached, the tracker system may issue a warning, eject or reject the cassette/pack and/or disable the surgical device from further use.

14 Claims, 15 Drawing Sheets

(51) Int. Cl.
   *A61B 90/96*     (2016.01)
   *A61B 90/98*     (2016.01)

(56) References Cited

U.S. PATENT DOCUMENTS

| | | | |
|---|---|---|---|
| 2006/0073048 A1* | 4/2006 | Malackowski | A61B 17/1626 417/474 |
| 2010/0249693 A1 | 9/2010 | Links | |
| 2015/0320948 A1 | 11/2015 | Eicher et al. | |

* cited by examiner

PHACOEMULSIFICATION SURGICAL MULTI-USE PACK USAGE TRACKER SYSTEM

BACKGROUND OF THE INVENTION

Field of Technology

The present invention relates generally to sensing usage of reusable cassettes/packs for surgical devices to determine if cassette/pack usage has reached a maximum number.

Description of the Background

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil and within a capsular bag, the capsular bag being a thin, relatively delicate structure which separates the eye into anterior and posterior chambers.

With age, clouding of the lens or cataracts is fairly common. Cataracts may form in the hard central nucleus of the lens, in the softer peripheral cortical portion of the lens, or at the back of the lens near the capsular bag. Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humor in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, aspiration flow systems can generally be classified in two categories: 1) volumetric-based aspiration flow systems using positive displacement pumps (e.g. peristaltic); and 2) vacuum-based aspiration systems using a vacuum source, typically applied to the aspiration flow through an air-liquid interface within a reservoir (e.g. Venturi). Both systems may be incorporated into one treatment system and/or cassette. Cassette ("pack") systems may be used to couple peristaltic pump drive rotors and/or vacuum systems of the surgical consoles to an eye treatment handpiece, with the flow network conduit of the cassette being disposable to avoid cross-contamination between different patients.

The disposable cassettes provide protection for each patient by avoiding cross-contamination between different patients. The disposable cassettes may be single-use, where the cassette is disposed after one use, or multi-use, where cassettes are reused after proper sterilization (e.g., autoclaving). In the case of multi-use phacoemulsification ("phaco") surgical packs, there is a maximum number of times a multi-use pack can or should be reused, as the pack quality deteriorates after certain amounts of usage and autoclave. Systems incorporating barcodes, such as one described in U.S. Pat. No. 6,036,458 to Cole et al., titled "Automated Phaco Pack Bar Code Reader Identification" issued Mar. 14, 2000, which is incorporated by reference herein, have been proposed to track usage and disposal of cartridges. However, such systems are not effective in accurately and consistently tracking usage for disposal purposes. Such systems are also not effective in accurately and consistently tracking a pack used on more than one system or machine. A mechanism to track how many times the cassette has been used is needed to ensure that it will not be used more than the recommended maximum number of times.

SUMMARY

Accordingly, in an exemplary embodiment, a reusable cassette sensing apparatus, configured to be part of a surgical device, is disclosed. The apparatus may comprise a film configured to indicate a maximum number of uses of the surgical device, and a tracking system comprising an implement, at least one sensor and a processor, wherein the implement is configured to engage with the film, and wherein the at least one sensor is configured to sense the maximum number of uses from the film, and, prior to use of the surgical device, the processor is configured to determine if the maximum number of uses has been reached based at least on a number of engagements of the implement with the film.

Under another exemplary embodiment, a method is disclosed for tracking usage of a reusable cassette, configured to be part of a surgical device, the method comprising the steps of sensing, prior to use of the surgical device, a maximum number of uses from a film configured to indicate a maximum number of uses of the reusable cassette; provided that the maximum number of uses has not been reached, activating an implement to engage with the film; and based at least in part on the implement's engagement with the film, determining a remaining number of usage for the reusable cassette. Alternatively, the film may be pre-cut with a number of apertures or holes, and wherein a single solid portion represents the last use, thereby determining that the cassette has been completely used when the implement engages with the solid portion instead of an aperture or hole.

Under another exemplary embodiment, a method is disclosed for tracking usage of the reusable cassette, configured to be part of the reusable cassette, where a "pinwheel" or wheel is divided into segments representing the maximum number of uses, and where an open hole or clear/light colored segment indicates available usage but a closed hole or dark/black color segment represents that the cassette/pack has reached its maximum use amount.

Under another exemplary embodiment, a method is disclosed for tracking usage of a reusable cassette, configured to be part of a surgical device, the method comprising the steps of advancing a pinwheel or wheel to a next segment when a cassette/pack is inserted into the device (based on idea of advancing film in camera), sensing the current usage count of the cassette through emission of light aimed at an open hole or clear/light segment of the pinwheel, and continuing to advance the pinwheel until the system senses a closed hole or dark/black segment indicating the maximum number of uses has been reached, the system using software to determine if the multi-use pack has reached its maximum usage.

Under another exemplary embodiment, a method is disclosed for tracking usage of the reusable cassette, configured to be part of the reusable cassette, where the tracking system includes a "rotating wheel/gear." The wheel/gear is divided into segments representing the maximum number of uses, where an open hole or clear/light colored segments indicate available usage, but a closed hole or dark/black color segment represents that the pack has reached maximum uses. When the method involves an open hole verses a closed hole, a probe or processor sensing resistance may be utilized to determine the segment. When the method involves a clear/light colored segment verse a dark/black colored segment, a sensor and/or light-emitting mechanism may be used.

Under another exemplary embodiment, a method is disclosed for tracking usage of a reusable cassette, configured to be part of a surgical device, the method comprising the steps of advancing a rotating wheel/gear through an axel rod residing in the instrument. The rod, when inserted, will turn and advance the wheel to the next segment when a pack is inserted. Alternatively, two or more gears may be used (e.g. one in the pack and one in the console or surgical device) to connect and turn or advance the wheel. The method further comprises sensing, through a light source such as an LED light, the current segment or spacing of the wheel. For example, the light may be aimed at the open hole or clear/light segments of the wheel when the cassette has not reached its maximum usage. The light may be aimed at the closed hole or dark/black segments of the wheel when the cassette has reached its maximum usage. The method includes software to determine if the multi-use pack has reached its maximum usage.

DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Figure 1:
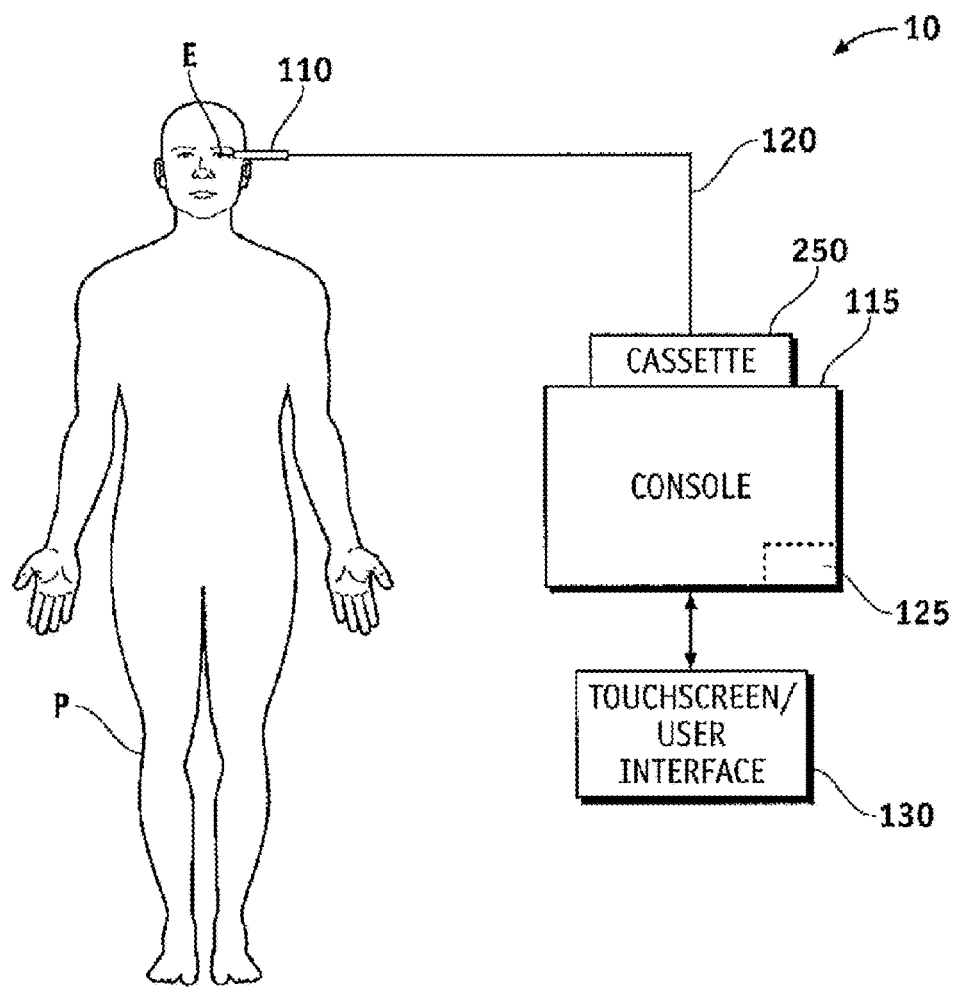
FIG. 1 is a schematic illustrating an embodiment of an eye treatment system in which a cassette is coupled to an eye treatment probe, the cassette being further coupled with an eye treatment console.

Referring now to FIG. 1, a system 10 for treating an eye E of a patient P generally includes an eye treatment probe handpiece 110 coupled with a console 115 by a cassette 250. Handpiece 110 generally includes a handle for manually manipulating and supporting an insertable probe tip (not shown). The probe tip has a distal end which is insertable into the eye, with one or more lumens (not shown) in the probe tip allowing irrigation fluid to flow from console 115 and/or cassette 250 into the eye E through an irrigation port connected to the lumen. The distal end of the probe tip may further include an aspiration port coupled to another lumen through which fluid may also be withdrawn or aspirated by way of an aspiration source. In an exemplary embodiment, the console 115 and cassette 250 may generally include a vacuum aspiration source, a positive displacement aspiration pump, or both to help withdraw and control a flow of surgical fluids into and out of eye E. As the surgical fluids may include biological materials that should not be transferred between patients, cassette 250 will often comprise a sterilizable (or alternatively, disposable) structure, with the surgical fluids being transmitted through flexible conduits 120 of cassette 250 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an irrigation/aspiration (I/A) and/or vitrectomy handpiece. Also, the ultrasonic transmitter may be replaced by other means for emulsifying a lens, such as a high energy laser beam. The ultrasound energy from handpiece 110 helps to fragment the tissue of the lens, which can then be drawn into the aspiration port of the tip by aspiration flow. In exemplary embodiments, it is preferable to maintain a certain amount of fluid within the eye E at all times during a surgical procedure. Accordingly, in order to balance the volume of fluid and material removed by the aspiration flow, an irrigation flow through handpiece 110 (or a separate probe structure) and through the irrigation port may also be provided, with both the aspiration and irrigation flows being controlled by console 115.

To avoid cross-contamination between patients without incurring excessive expenditures for each procedure, cassette 250 and its flexible conduits 120 may be disposable. In other embodiments, the flexible conduit or tubing 120 may be disposable, while the cassette body 250 and/or other structures of the cassette 250 are sterilizable and/or reusable. Cassette 250 may be configured to interface with reusable components of console 115, including, but not limited to, peristaltic pump rollers, a Venturi or other vacuum source, a controller 125, and/or the like, as discussed below.

As illustrated in FIG. 1, console 115 may include a controller 125. Controller 125 may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 may often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader (not shown), or the code may be transmitted to controller 125 by a network connection such as an internet, an intranet, an Ethernet™, a wireless network, or the like. Along with programming code, controller 125 may include stored data for implementing the methods described herein, and may generate and/or store data that records parameters corresponding to the treatment of one or more patients. Many components of console 115 may be found in or modified from known commercial phacoemulsification systems from Abbott Medical Optics Inc. of Santa Ana, and other suppliers.

Figure 2:
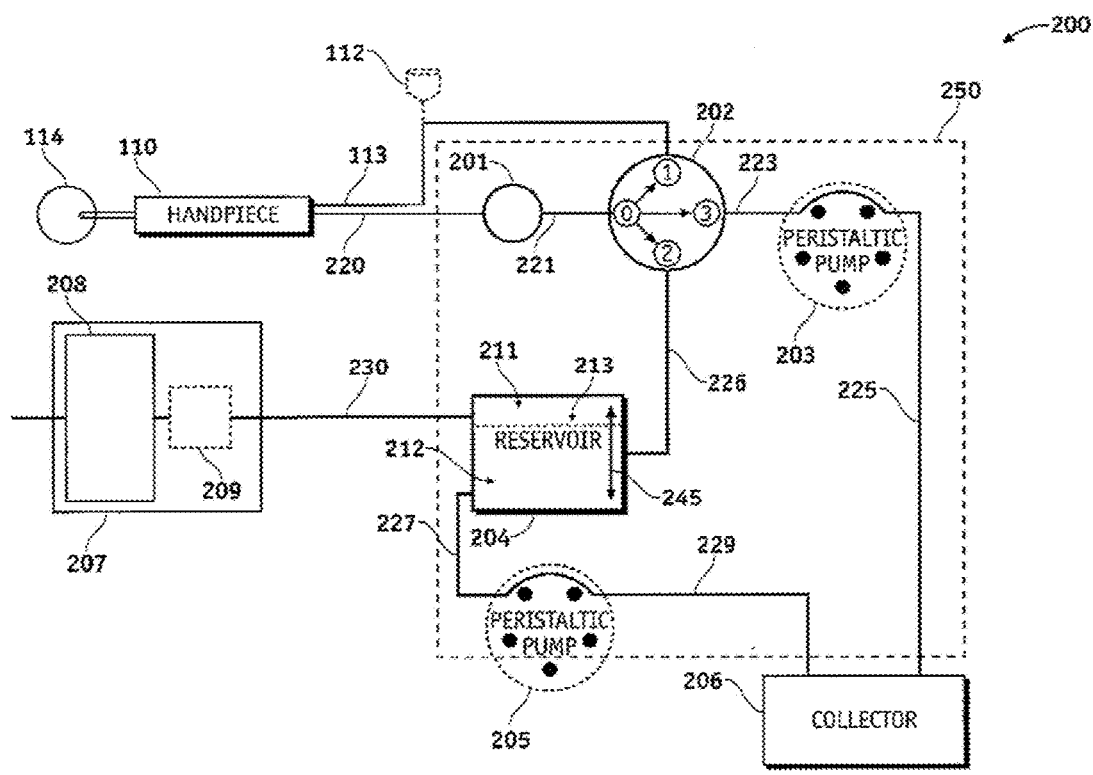
FIG. 2 is a functional block diagram of an exemplary cassette system under one embodiment, the cassette system being connected to a handpiece, a vacuum pump arrangement and a collector.

Referring to FIG. 2, an exemplary cassette system 200 showing some of the components and interfaces that may be employed in a phacoemulsification system. In illustrative embodiments, the cassette system 200 includes, for example, the cassette 250, which further includes, for example, a vacuum sensor 201, a flow selector valve 202, one or more pumps 203/205, and a reservoir 204. Handpiece 110 is connected to (or coupled with) the input side of fluid vacuum sensor 201, typically by conduits 120. In illustrative embodiments, the conduits 120 may comprise fluid pathways such as a fluid pathway 220. The output side of fluid vacuum sensor 201 is connected to flow selector valve 202 within cassette 250 via a fluid pathway 221. The present design may configure flow selector valve 202 to interface between handpiece 110, a balanced saline solution (BSS) fluid bottle 112, a first pump 203 (which is shown as a peristaltic pump but may be another type of pump), and reservoir 204. In various embodiments, flow selector valve 202 may connect with fluid bottle 112 via a flow pathway (between 202 and 112), flow selector valve 202 may connect with pump 203 via a flow pathway 223, and flow selector valve 202 may connect with reservoir 204 via a flow pathway 226. In this configuration, the system may operate flow selector valve 202 to connect handpiece 110 with BSS fluid bottle 112, reservoir 204 or with pump 203 based on signals received from console 115 resulting from the surgeon's input to user interface 130 or any other system input device.

In illustrative embodiments, the flow selector valve 202 illustrated in FIG. 2 provides a single input port '0', and may further connect port '0' to one of three available ports numbered '1', '2', and '3'. The present design is not limited to one flow selector valve, and may be realized using two flow selector valves each having at least two output ports, possibly connected together to provide the functionality described herein. For example, a pair of two output port valves may be configured in a daisy chain arrangement, where the output port of a first valve is directly connected to the input port of a second valve. Console 115 may operate both valves together to provide three different flow configurations. For example, using two valves, a first valve may include at least a first output port and a second outlet port, with the first output port being the supply for a second valve. The second valve may connect to one of two outlet ports to provide two separate paths. When the first valve connects its input port to its second output port rather than the first output port, a third path is provided. Other means of providing multiple outlet ports are well known in the industry. Further, it is envisioned that a cassette system 200 may require more than three outlet paths and that a variety of flow selector valves or a series of flow selector valves that can create the desired number of outlet paths are well known in the industry.

It is also envisioned that flow selector valve 202 may be or comprise one or more pinch valves (not shown). As an illustrative example, the one or more pinch valves may be located along fluid pathway 221 and/or 223, or any other fluid pathway as discussed herein. Further, there may be one or more fluid pathways coupled with handpiece 110 and extending to various components of cassette 250. In another embodiment, fluid pathway 220 from handpiece 110 is a single fluid pathway that couples with fluid vacuum sensor 201. In certain embodiments, there are multiple pathways within cassette system 200, including a first fluid pathway from fluid vacuum sensor 201 to collector 206 via pump 203 and/or a second fluid pathway from vacuum sensor 201 to reservoir 204. From fluid vacuum sensor 201, the single fluid pathway 220 may divide into two fluid pathways, one to collector 206 via pump 203 and one to reservoir 204. Further, one or more pinch valves and/or flow selector valve 202 may be located along the fluid pathway between fluid vacuum sensor 201 and collector 206 and/or between fluid vacuum sensor 201 and reservoir 204.

Thus while a single flow selector valve 202 is illustrated in FIG. 2, it is to be understood that this illustration represents a flow selector valve arrangement, including one or more flow selector valves performing the functionality described herein, and is not limited to a single device or a single flow selector valve.

In illustrative embodiments, the fluid vacuum sensor 201 may include, for example, a strain gauge or other suitable component, that communicates or provides signal information to console 115 to provide the amount of vacuum sensed in the fluid pathway 220 or, more particularly, in one or more lumens within the handpiece 110. Console 115 may determine the actual amount of vacuum present based on the communicated information.

Fluid vacuum sensor 201 monitors flow into and out of the handpiece 110, and can be used to determine when flow should be reversed, such as encountering a certain pressure level (e.g. in the presence of an occlusion). Based on values or information obtained from the fluid vacuum sensor 201, the console 115 or another part of the system may control selector valve 202 and the pump(s) 203/205, as illustrated. It is to be understood that while components presented in FIG. 2 and other drawings of the present application are not shown connected to other system components, such as console 115, they are in fact connected for the purpose of monitoring and controlling of the components illustrated.

As discussed previously, it may be desirable to maintain or control the amount or pressure of fluid flowing into or out of the eye E during a surgical procedure. With respect to fluid vacuum sensor 201, emergency conditions, such as a dramatic drop or rise in pressure as determined by fluid vacuum sensor 201, may result in a type of fail-safe operation being employed. The present design employs fluid vacuum sensor 201 to monitor the flow conditions and provide signals representing flow conditions to the system, such as via console 115, for the purpose of controlling components shown, including but not limited to flow selector valve 202 and the pumps 203/205 shown. The fluid pathways or flow segments of surgical cassette system 200 may include fluid connections, for example flexible tubing, between each component represented with solid lines in FIG. 2.

In illustrative embodiments, cassette system 200 is coupled to a vacuum pump arrangement 207. In other embodiments, vacuum pump arrangement 207 may be integral with cassette system 200. Vacuum pump arrangement 207 is typically coupled with console 115, and may be connected with reservoir 204 via a fluid pathway or flow segment 230. In the configuration shown in FIG. 2, vacuum pump arrangement 207 includes a pump 208, such as a venturi pump, and an optional pressure regulator 209 (and valve (not shown)), but other configurations for the pump arrangement 207 are possible. In this arrangement, vacuum pump arrangement 207 may operate to remove air from the top of reservoir 204 and deliver the air to atmosphere (not shown). Removal of air from reservoir 204 in this manner may reduce the pressure within the reservoir 204, causing an air-fluid boundary 213 in reservoir to move upward. This reduction in pressure will cause a reduction in the pressure in the fluid pathway 226 coupled to the reservoir 204. In illustrative embodiments, the pressure in fluid pathway 226 may be reduced to a level less than the pressure within eye 114. A lower pressure in fluid pathway 226 (from a lower pressure in reservoir 204) connected to flow selector valve 202 may cause fluid to move through the upstream pathways of flow selector valve 202, including pathway 221 and 220, from the eye 114. Accordingly, the lower pressure in reservoir 204 may cause fluid to move from the eye 114 via fluid pathway 220, thereby providing aspiration. The vacuum pump arrangement 207 and reservoir 204 can be used to control fluid flow into and out of reservoir 204.

Conversely, the optional pressure regulator 209 may operate to add air to the top of reservoir 204 which in turn increases pressure and may force the air-fluid boundary 213 to move downward. Adding air into reservoir 204 in this manner may increase the air pressure within the reservoir 204, which increases the pressure in the attached fluid aspiration line 226. In illustrative embodiments, the pressure in the fluid aspiration line 226 may be increased to a level greater than the pressure within eye 114. A higher reservoir pressure connected through flow selector valve 202 may cause fluid to move toward eye 114, thereby providing venting or reflux. Other means for providing venting or reflux are well known in the art.

The present design may involve peristaltic operation—aspirating fluid from the eye 114 to collector 206 as illustrated in FIG. 2—or venting operation—venting fluid to the eye 114 to reduce the amount of pressure in an aspiration line (where such venting is shown, for example, from BSS bottle 112 in FIG. 2). Peristaltic pumping is generally understood to those skilled in the art, and many current machines employ peristaltic and/or venturi pumps as the vacuum or pressure sources. Generally, a peristaltic pump has fluid flowing through a flexible tube and a circular rotor with a number of rollers attached to the periphery of the circular rotor. As the rotor turns, fluid is forced through the tube. Venturi pumping, or aspiration or aspirator pumping, produces the vacuum using the Venturi effect by providing fluid through a narrowing tube. Because of the narrowing of the tube, the speed at which the fluid travels through the tube increases and the fluid pressure decreases (the "Venturi effect"). As may be appreciated, operating pumps in one direction or another can change the pressure and the operation of the associated device, such as the operation of the cassette in the present design.

Figure 2A:
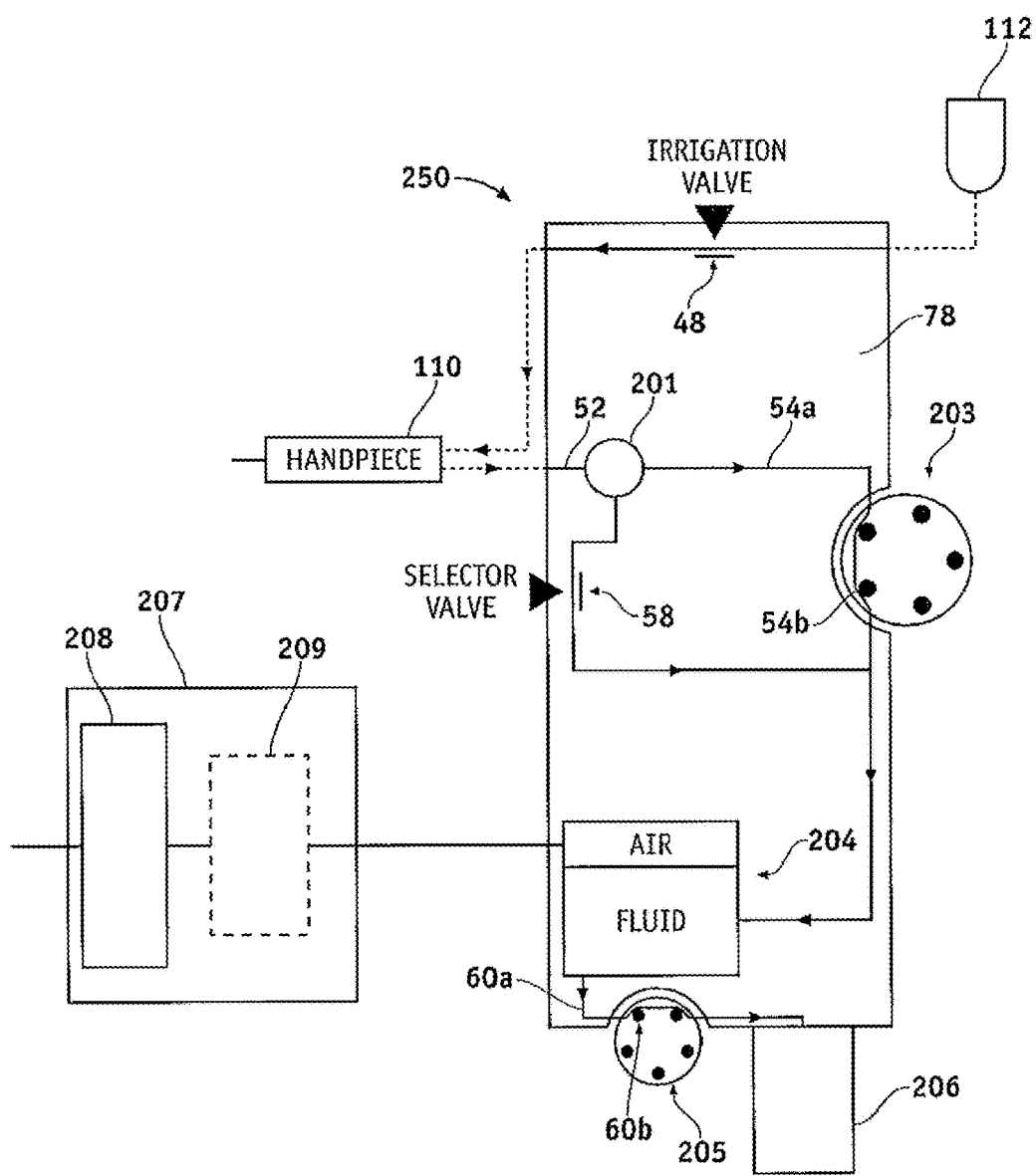
FIG. 2A is another functional block diagram of an exemplary cassette system under one embodiment, the cassette system being connected to a handpiece, a vacuum pump arrangement and a collector.

Referring now to FIG. 2A, another system is illustrated. FIG. 2A generally highlights the surgical aspiration and irrigation fluid control elements included within the cassette 250 and console 115. The irrigation components are often relatively straightforward and known in the industry. A BSS fluid bottle 112 or the like connected to console 115 optionally provides irrigation fluid pressure control by relying at least in part on a gravity pressure head that varies with a height of BSS fluid bottle 112. An irrigation on/off pinch valve 48 may generally include a short segment of a flexible conduit lumen (e.g. 113 of FIG. 2) of or coupled to cassette 250, which can be engaged and actuated by an actuator (not shown) of console 115. A surface of cassette body 78 may be disposed opposite the actuator to facilitate closure of the conduit lumen. Alternative irrigation flow systems may include positive displacement pumps, alternative fluid pressurization drive systems, fluid pressure or flow modulating valves, as discussed above, and/or the like.

FIG. 2A further illustrates the aspiration components. Aspiration flow path 52 couples an aspiration port (not shown) in the tip of handpiece 110 with pump 203 and/or a reservoir 204. Fluid aspirated through handpiece 110 may be contained in reservoir 204 regardless of whether the aspiration flow is induced by pump 203 or vacuum pump arrangement 207. For instance, when a selector control valve 58 positioned between vacuum fluid sensor 201 and reservoir 204 is closed and pump 203 is in operation, pumping of the aspiration flow may generally be directed by the pump 203, independent of the pressure in the reservoir 204. In such case, the aspiration flow may flow through conduit 54a. Conversely, if pump 203 is a peristaltic pump and is off, flow through the pump 203 may be halted by pinching of the elastomeric tubing arc of the peristaltic pump by one or more of the individual rollers of the peristaltic pump rotor (similar to the rollers of 60b in pump 205). Hence, any aspiration fluid drawn into the aspiration network (fluid pathways) when pump 203 is off will typically involve the opening of selector control valve 58 so that the aspiration port of the probe or handpiece 110 is in fluid communication with reservoir 204. Alternatively, communication with vacuum pump arrangement 207 may be accomplished by disengaging the peristaltic probe drive from the elastomeric tubing. The pressure within reservoir 204 may be maintained at a controlled vacuum level, often at a fixed vacuum level, by vacuum pump arrangement 207. Vacuum pump arrangement 207 may comprise a vacuum (e.g. Venturi) pump, a rotary vane pump, a vacuum source, pressure regulator, or the like. Aspiration fluid that drains into reservoir 204 may be removed by pump 205 and directed to collector 206 via a fluid pathway 60a. Vacuum pressure at the surgical handpiece 110 may be maintained within a desired range through control of the fluid level in reservoir 204.

Figure 2B:
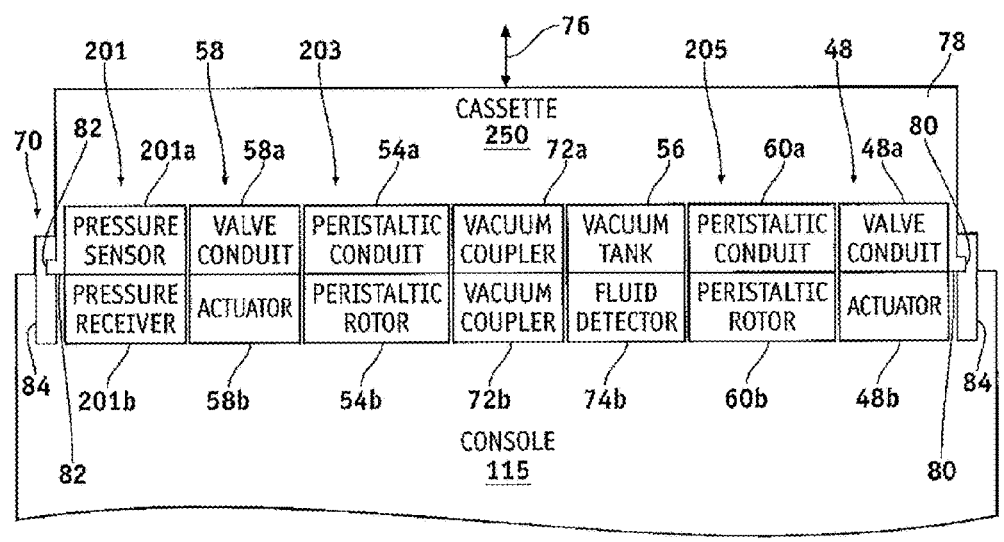
FIG. 2B is a schematic illustrating detailed elements of a cassette system and eye treatment console as shown in FIG. 1.

Referring now to FIG. 2B, an interface 70 between cassette 250 and console 115 is schematically illustrated. Many of the fluid network structures described above regarding FIGS. 2 and 2A include or make use of corresponding elements of cassette 250 and the console 115. For example, with respect to FIG. 2A, fluid vacuum sensor 201 may be included in a pressure sensing system which includes a pressure sensor 201a in cassette 250 having a pressure chamber (not shown) and a surface (not shown) that moves in response to variations in the pressure in the chamber. Axial movement of the pressure sensor surface may be determined using a pressure receiver 201b which may be incorporated into console 115. In the exemplary embodiments, direction of movement of the pressure sensor surface may be aligned with a mounting axis 76 of cassette 250, representing a direction of movement of cassette 250 during mounting of cassette 250 to console 115.

Similarly, other components of cassette 250 and console 115 may be predetermined to engage with each other about interface 70. Selector valve 58 may make use of a resilient valve conduit 58a in cassette 250 that is engaged by an actuator 58b of console 115. As described above, pump 203 may include a conduit 54a of cassette 250 engaged by a peristaltic rotor 54b of console 115, with the interface 70 effecting engagement between the conduit 54a and the peristaltic rotor 54b. A vacuum coupler 72a of cassette 250 may engage a vacuum coupler 72b of console 115 so as to allow vacuum pump arrangement 207 to apply a vacuum to reservoir 204 (See FIG. 2A). Reservoir 204 may be coupled with a fluid detector 74b of console 115 using a mechanical, electrical, or light fluid presence detector system so as to allow controller 125 of console 115 to determine when it is appropriate to energize pump 205. Rather than simply detecting the presence of fluid, alternative embodiments might employ a more complex fluid level sensing system which determines a quantity or volume of fluid in the tank for purposes of selectively energizing pump 205. Pump 205 includes a conduit 60a of cassette 250 and a peristaltic rotor 60b of console 115. Irrigation valve 48 may include a resilient valve conduit 48a of cassette 250 and a valve actuator 48b of console 115. Other components—electrical, mechanical, or otherwise—may be predesigned to engage with each other from the cassette 250 and the console 115.

Engagement and alignment between cassette 250 and the interfacing structures of console 115 may be achieved through a variety of mechanisms, some of which are described in U.S. Pat. No. 8,491,528 to Muri et al., titled "Critical Alignment of Fluidics Cassettes" issued Jul. 23, 2013 and U.S. Pat. Pub. No. 2010/0249,693 to Jeremy T. Links, titled "Cassette Capture Mechanism," filed Mar. 31, 2009, each of which are incorporated by reference in their entirety herein. A cassette 250 may generally have a height and a width which generally are greater than a thickness of cassette 250 along a mounting axis, allowing the interfacing fluid pathway network elements of cassette 250 and corresponding components of console 115 to be distributed in a roughly planner configuration. In addition to the individual interfaces, cassette 250 may generally include a cassette body 78 with positioning surfaces 80 that engage corresponding with cassette receptacle surfaces 82 of console 115. Cassette receptacle surfaces 82 define a cassette receptacle 100 that receives and positions cassette 250. In one exemplary embodiment, cassette 250 is manually supported and advanced along mounting axis 76 until positioning surfaces 80 engages and deflects an alignment switch 84 of console 115. One or more alignment switches may be used; preferably two alignment switches are employed with a cassette receptacle on console 115. The alignment switch may be a pin/flag, optical, magnetic, or any other detection mechanism known in the art.

In various embodiments, a cassette may be designated for a predetermined or set number of uses before it should be disposed of and replaced with a new cassette. In the present disclosure, the number of usages of a particular cassette 250 may be determined or tracked in order to ensure a specific cassette 250 is not utilized past its predetermined usage amount. Such tracking is beneficial to avoid overuse of a cassette that could cause undesired effects, such as unintentional contamination from previously aspirated materials, during a surgical procedure. In various embodiments, the number of predetermined uses will be dependent on the size and functionality of the cassette 250. For instance, a particular cassette may require disposal after a maximum of 15-30 uses. A variety of cassettes with varying maximum use requirements are known in the industry.

Figure 3:
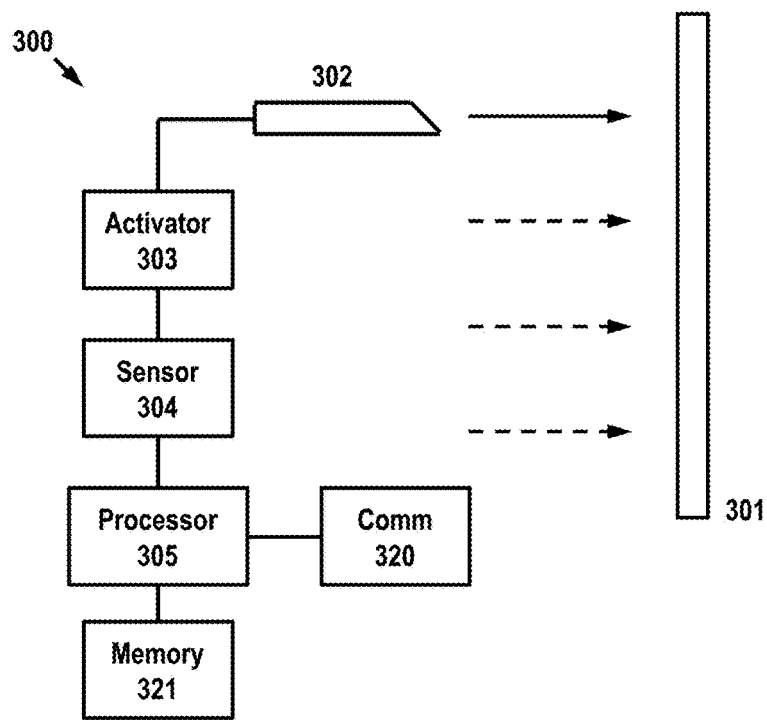
FIG. 3 illustrates an exemplary cassette tracking system for determining cassette usage under one embodiment, the cassette tracking system including a film usage system and film.

Turning to FIG. 3, an exemplary embodiment is provided where a usage tracking system 300 interacts with a film 301 for tracking cassette usage. In one embodiment, film tracking system 300 and film 301 are configured to be inside a cassette 250 to avoid potential contamination and/or damage. In another embodiment, tracking system 300 and film 301 may be configured separately from the cassette 250. For example, system 300 and film 301 may be encased in a separate housing (not shown) that is cooperatively attachable to a cassette 250. In another embodiment, film tracking system may be configured to be inside console 250 and film 301 may be configured to be inside or coupled with cassette 250. As noted previously, the usage tracking system 300 may be configured to permit adequate tracking of the number of uses of a cassette even when the cassette has been removed from one system and incorporated into another system. It should be understood by those skilled in the art that a specific cassette/pack incorporating usage tracking system 300 may comprise greater or fewer internal components that those listed herein.

As can be seen in FIG. 3, system 300 may comprise an implement or probe 302 suitable for physically interacting with film 301. In one embodiment, implement 302 may comprise a punch or similar structure that penetrates through the surface of film 301. In another embodiment, implement 302 may comprise a blade for cutting through a portion of film 301. In a still further embodiment, implement 302 may comprise a marking implement that ejects ink or electrically conductive ink onto the surface of film 301. In a still further embodiment, film 301 may comprise photoreactive material that discolors or otherwise reacts to light illumination, and the implement 302 may include a light source or other light-emitting feature that shines onto the photoreactive material. It should be understood by those skilled in the art that other types of implements are envisioned through the present disclosure.

Implement 302 is operatively coupled to an activator 303, which causes implement 302 to punch/cut/mark/effect film 301. Activator 303 may further comprise a mechanism and circuitry to provide a linear force along a plane covering the area of film 301 (shown as arrows in FIG. 3) to provide punching, cutting, marking, etc of film 301. In the case of a marker implement, activator 303 may be integrated as part of implement 302 and provide the mechanism and activation for implement 302 to provide ink onto the surface of film 301. In the case of a light-emitting implement, activator 303 may further provide the mechanism and circuitry for emitting light onto the surface of film 301.

Figure 3A:
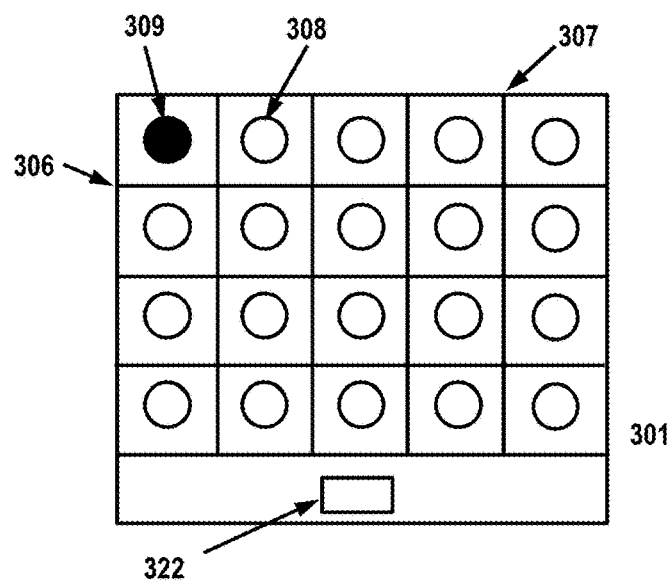
FIG. 3A illustrates an exemplary film for tracking cassette usage under the embodiment of FIG. 3, wherein a punch system for tracking the number of uses of the cassette.

In various embodiments, film 301 may be partitioned into predetermined spaces (e.g. boxes in FIG. 3A). The predetermined spaces may be determined to represent the maximum number of uses of the cassette 250. Implement 302 may be configured to punch/cut/mark/effect a single space on film 301 with every use of the cassette 250. Activator 303 may be coupled to a sensor 304 which may be configured to optically and/or electrically sense remaining, unmarked or un-illuminated spaces left on film 301, thereby indicating the number of remaining uses left for a particular cassette 250. Accordingly, the number of remaining uses for a cassette 250 may be tracked and determined by the system in order to ensure the cassette 250 does not exceed its maximum number of uses.

Sensor 304 may further comprise a secondary sensor capable of detecting film configuration data provided by a film code 322 on film 301, explained further in detail below in connection with FIG. 3A. In illustrative embodiments, sensor 304 is operatively coupled to a processor 305 and a memory 321, which may provide operational instructions for operating activator 303 or implement 302. System 300 may further comprise a communication system 320, which may allow system 300 to send/receive data, preferably via a wireless communication data link. Exemplary communication systems include, but are not limited to, Bluetooth, WiFi, cellular, RFID, and near field communication (NFC). Under one exemplary embodiment, operational parameters for sensor 304 and/or activator 303 may be communicated to processor 305 via communication system 320. Similarly, data obtained from sensor 304 or implement 302 may be communicated externally as well.

As illustrated in FIG. 3, when a particular cassette is engaged and used for a first time, sensor 304 may scan and sense a maximum number of allowable uses for the cassette from a film code 322 (shown in FIG. 3A) on film 301. Upon first use of the cassette, processor 305 may engage activator 303 to cause implement 302 to punch film 301 (indicated by solid arrow in FIG. 3). Prior to each subsequent use, sensor 304 may scan and sense the remaining uses (indicated by remaining spaces on film 301), and provided remaining uses are available, processor 305 may engage activator to cause implement 302 to punch film 301 each time another use takes place (indicated by dotted arrows in FIG. 3). When no further uses are available, processor 305 may send a "disposal" signal to indicate no further uses are available. This signal may comprise a warning signal that may optically indicate (e.g. LED light) or audibly indicate (e.g., via speakers) that the maximum number of uses have been reached. The signal may also comprise a shut-down signal that disallows further use of the device until another cassette is installed. The signal may also comprise an eject signal, which causes one or more actuators to eject the cassette and not allow re-engagement of the same cassette. Other means for sending such a disposal signal are well known in the industry.

Turning now to FIG. 3A, an exemplary embodiment is provided of a film 301 configured to be used in the embodiment of FIG. 3. Here, film 301 may be segmented into a plurality of rows 306 and columns 307 containing an area or space 308 wherein implement 302 may engage. Under one exemplary embodiment, the segmentation of rows 306 and columns 307 allows sensor 304 to scan the area of the film to determine what areas were already punched/cut (309) and/or the spaces remaining that have not been punched/cut (adjacent arrow 308). Of course, as described above, a similar configuration may be implemented for ink markings or light emitting as well. It should also be appreciated by those skilled in the art that, while a grid configuration of spaces 308 has been disclosed, other physical configurations, such as a linear strip or single row 306 of spaces 308, are envisioned as well.

Under one exemplary embodiment, a film identifier or code 322 may be used that provides information on the film 301 and the number of maximum uses available. In one embodiment, film identifier 322 comprises a bar code, QR code, or the like. In another embodiment, film identifier 322 comprises an RFID tag, or similar communication protocol. Thus, when film 301 is engaged with system 300, a scan from sensor 304 of film identifier 322 would indicate, for example, that film 301 is configured to allow X number of uses. Such information would then be conveyed to processor 305. After each use, processor 305 could simply count down automatically the remaining uses until a maximum is reached, and thereafter send the "disposal" signal as described above.

Figure 3B:
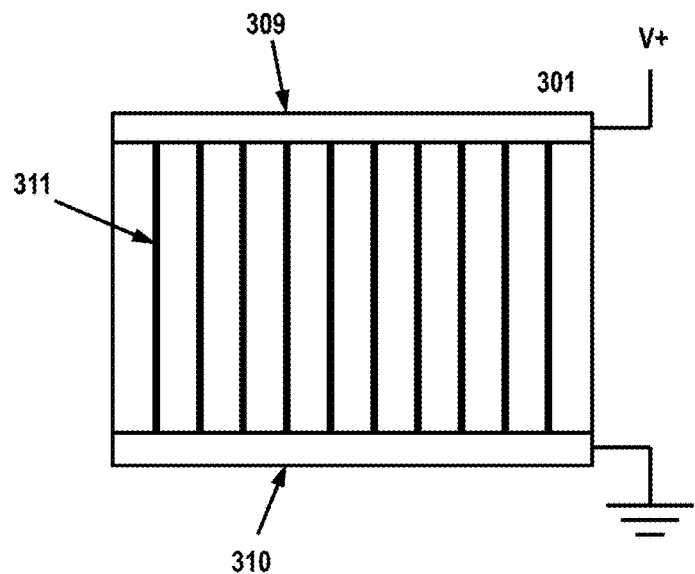
FIG. 3B illustrates another exemplary film for tracking cassette usage under the embodiment of FIG. 3, wherein conductive threads between a voltage source and ground may be selectively cut to track the number of uses of the cassette.

Turning to FIG. 3B, another exemplary embodiment of a usage tracking system 300 is provided where a film 301 comprises a plurality of conductive threads 311 coupled between a voltage area 309 and ground 310. The system of FIG. 3B may include similar components as discussed above. In this example, implement 302 may be configured to cut each thread 311 of film 301 after each use of the cassette.

The voltage area 309 or ground 310 may be electronically coupled to the sensor 304 such that the sensor 304 can determine the number of cut or full-length threads 311 on film 301. Accordingly, the remaining threads 311 on film 301 would indicate the number of remaining uses left, thereby permitting the processor 305 coupled to the sensor 304 to track uses of the cassette.

Figure 4:
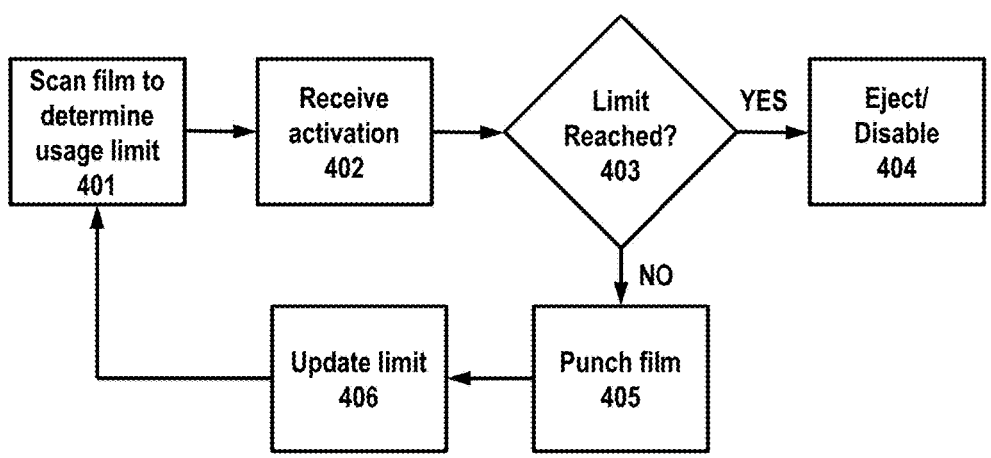
FIG. 4 illustrates an exemplary process for determining and restricting cassette usage under one embodiment.

FIG. 4 illustrates an exemplary method of using the configuration illustrated in FIG. 3 and/or in other embodiments disclosed herein. In step 401, system 300 scans film 301 to determine the number of uses allowed (usage limit). The scan may comprise an electrical/optical scan of the film 301 surface, or voltage readings in the voltage area 309 or ground 310, by sensor 304, and/or information provided by identifier 322. In step 402, use of a surgical device provides activation 402, wherein system 300 determines if a limit has been reached 403. If the maximum number of uses has been already reached, system 300 provides an eject/disable/warning/disposal signal 404 to warn or prevent further usage. If, in 403, remaining uses are available, activator 303 may cause implement 302 to punch 405 (or otherwise mark or effect) film 301. The cassette may thereafter be used during a surgical operation. Afterwards, the usage limit may be updated 406 to reflect the recent usages, and, upon subsequent uses, scan 401 may be repeated. The process may continue numerous times until a limit in step 403 has been reached.

Figure 5A:
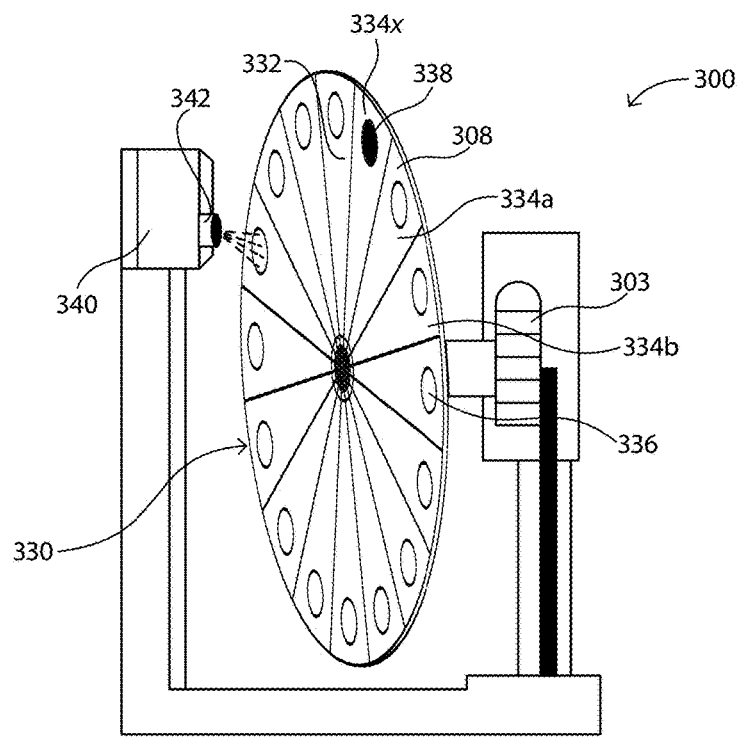
FIG. 5A illustrates a side perspective view of another exemplary cassette tracking system for determining cassette usage, the cassette tracking system including a rotatable wheel and sensing mechanism to track the rotation of the wheel.
Figure 5B:
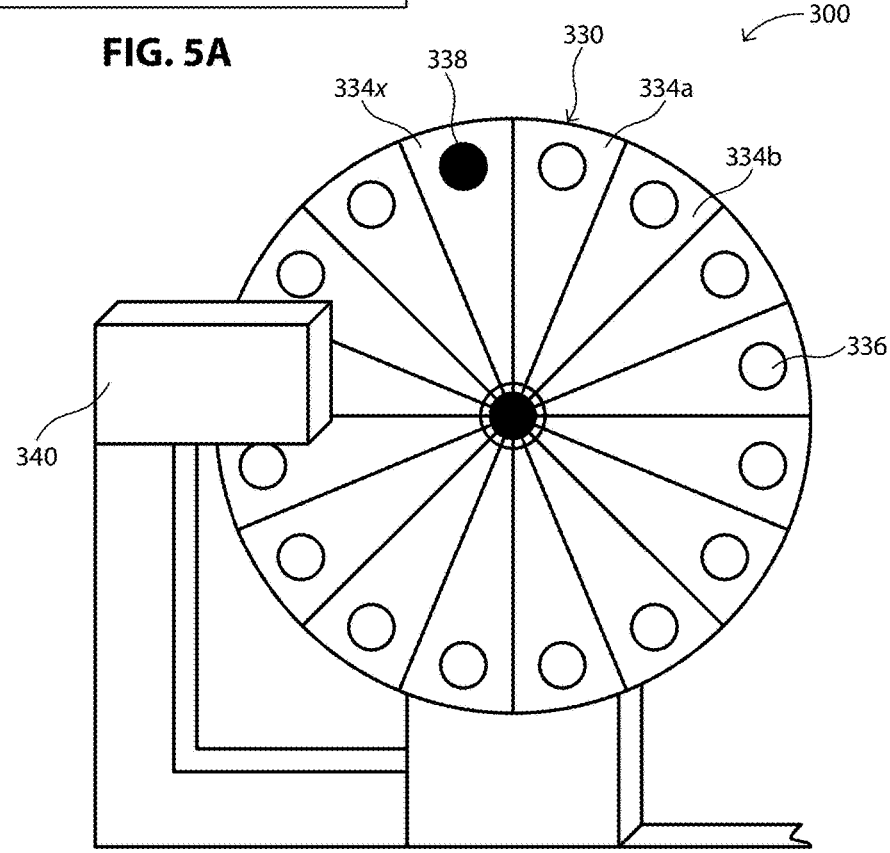
FIG. 5B illustrates a front perspective view of the cassette tracking system of FIG. 5A.

Turning to FIGS. 5A and 5B, another exemplary embodiment of a usage tracking system 300 is provided including a pinwheel or wheel 330 and a reader 340. Although not shown in FIGS. 5A and 5B, the wheel 330 may be coupled to an activator 303 as described above such that the activator 303 can control the wheel 330 based input from the sensor 304 and/or processor 305. In illustrative embodiments, the wheel 330 may be located in a cassette and is configured to advance or rotate a specific amount of degrees with every use of the cassette. In addition in an embodiment, the other components of the usage tracking system 300 may be located in the console 115. As illustrated in FIG. 5B, a surface 332 of the wheel 330 may be partitioned or divided in order to provide predetermined spaces 308 that corresponds with the number of maximum uses of the cassette. As an example, this may be accomplished by dividing the wheel 330 into pie-sized sections 334, or any other suitable shape. As the wheel 330 rotates, each section 334 a, 334 b, etc, include a light or white color segment 336, except the last section 334 x may include a black or dark color segment 338. The reader 340 may be fixedly positioned to read a different section 334 as the wheel 330 rotates. In illustrative embodiments, the reader 340 may include optical sensors 342 or provide a sensing mechanism through resistance in the console. As the wheel advances around for each use of the cassette, the sensors 342 will detect the white or light colored segments 336 until the wheel 330 rotates to place the black or dark colored segment 338 in line with the sensor 342. When the reader 340 reads the black or dark color segment 338, then the cassette pack can no longer be used and the processor 205 may send the "disposal" signal to the system.

Figure 6:
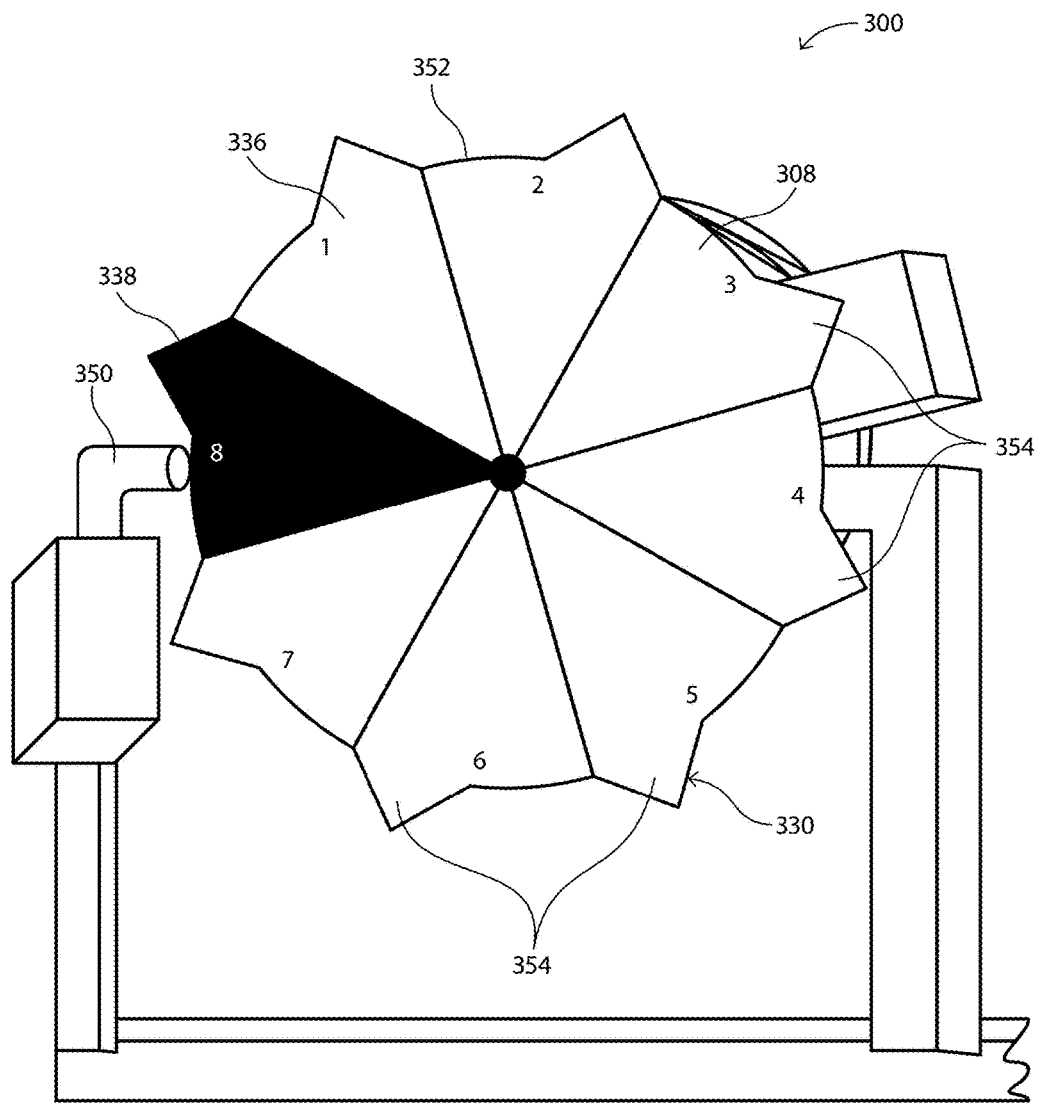
FIG. 6 illustrates a front perspective view of another exemplary cassette tracking system for determining cassette usage, the cassette tracking system including a rotatable wheel with variations and a sensing mechanism to track rotation of the wheel.

Turning to FIG. 6, another exemplary embodiment of a usage tracking system 300 is provided including a wheel 330 and a pinion 350 is illustrated. As discussed above with regard to FIGS. 5A and 5B, the wheel 330 may be coupled to an activator 303 as described above such that the activator 303 can control the wheel 330 based on input from the sensor 304 and/or processor 305. In illustrative embodiments, the wheel 330 may be located in a cassette and is configured to advance or rotate a specific amount of degrees with every use of the cassette. In addition in an embodiment, the other components of the usage tracking system 300 may be located in the console 115. As illustrated in FIG. 6, the wheel 330 may be partitioned or divided into substantially equal segments 336 and 338 that correspond with the number of maximum uses of the cassette. The wheel 330 may include an edge 352 that surrounds and aligns with the segments 336 and 338. Each segment 336 and 338 may include an outwardly extending protrusion 354, as illustrated in FIG. 6.

The pinion 350 may be configured to abut against or be biased against the edge 352 of the wheel 330. As the wheel 330 advances or rotates due to use of the cassette, the pinion 350 rides up and over the extending protrusion 354 of the segment 336 to sit or abut against the next segment 336. When the pinion 350 abuts against the last segment 338, the wheel 330 may be prevented from further rotation. Alternatively, the last segment 338 may include black or dark coloring, and the pinion 350 may include a reader (similar to 340) that can detect the color change, as discussed above. In such a way, the usage tracking system 300 may operate similar to a camera advancing mechanism where the pinwheel 330 rotates clockwise/counter-clockwise with each advancement to catch the spokes or protrusions of the wheel. Similar sensing mechanisms as discussed in paragraph above.

In another embodiment, the usage tracking system 300 may be like film in a camera where it continues to turn until the film runs out, thereby making it such that the wheel can no longer turn. When this occurs, the maximum number of uses for that cassette has been reached and the cassette can no longer be used.

Figure 7:
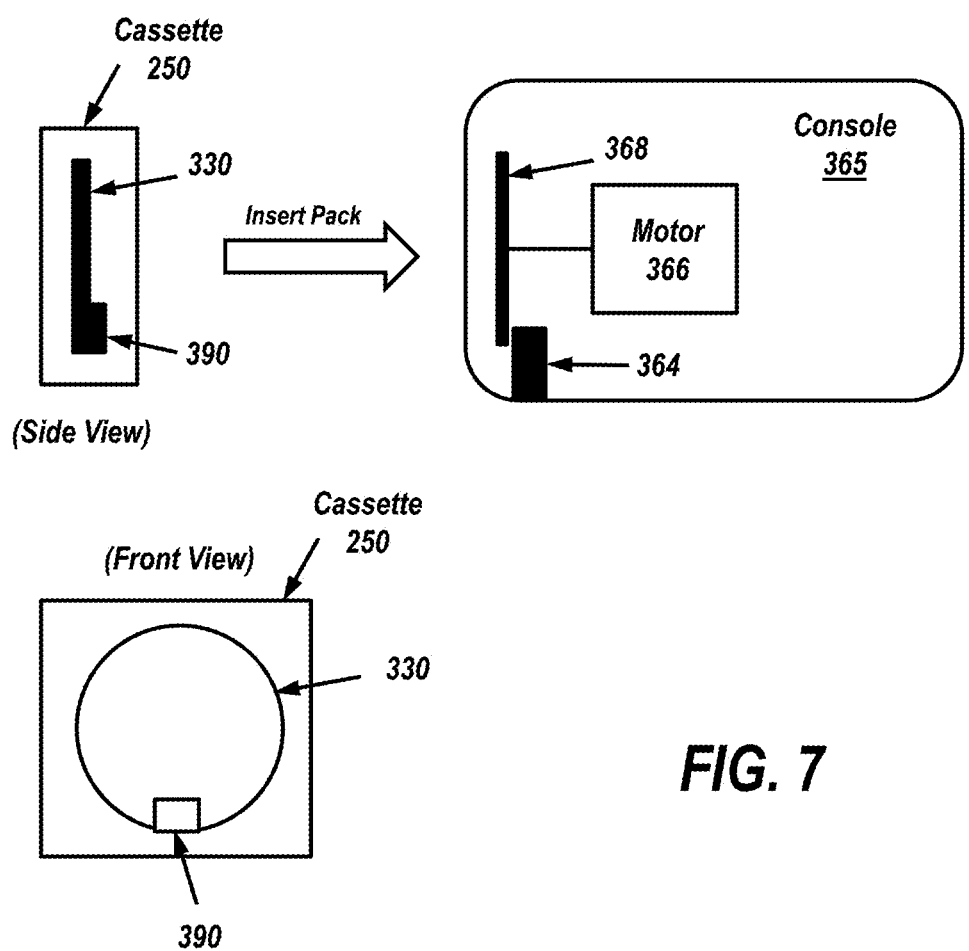
FIG. 7 illustrates another exemplary cassette tracking system for determining cassette usage, the cassette tracking system including a rotating track with a latch that mates with a rotatable wheel to rotate the wheel to a predetermined position, the wheel further including a protrusion that prevents the latch from further rotation at the predetermined position.

Turning to FIG. 7, another exemplary embodiment of a usage tracking system 300 is provided. In this example, protrusion 390 is provided to a portion (e.g., underside) of wheel 330 of cassette 250, that may be inserted into console 365. Console 365 may be configured with a motor 366 arranged to turn/rotate track 368, and may further include structure 364 protruding on the console side. Motor 366 may be configured to turn/rotate track 368 freely, or may be configured to turn/rotate track 368 in a controlled manner (e.g., a predetermined amount of rotation(s); rotating the track a predetermined amount for each rotation, etc.). After a full rotation, protrusion 390 will come into contact with structure 364, which will impede further movement, indicating the pack has been used a maximum number of times.

When a new pack or cassette 250 is inserted, the pack may be configured such that protrusion 390 is positioned in the same position each time, such as the position illustrated in the front view of FIG. 7. After insertion, the wheel 330 and track 368 may couple such that rotational force provided by motor 366 causes wheel 330 to rotate via the track 368. In one example, the rotational distance may be divided into a predetermined number of evenly spaced intervals (e.g., 20 intervals) corresponding to respective cassette usages. After the final interval has turned, the following interval (e.g., beginning of the $21^{st}$ interval) will cause the protrusion 390 to come into contact with structure 364, and thus preventing further rotation. In one illustrative embodiment, the blocking of rotation in the wheel may cause the cassette system (e.g., 200) to generate a signal indicating that the cassette is not valid. In another illustrative embodiment, protrusion 390 and structure 364 may be manufactured from a conductive material such that physical contact may cause an electronic circuit to close, indicating the cassette should not be used further.

Figure 7A:
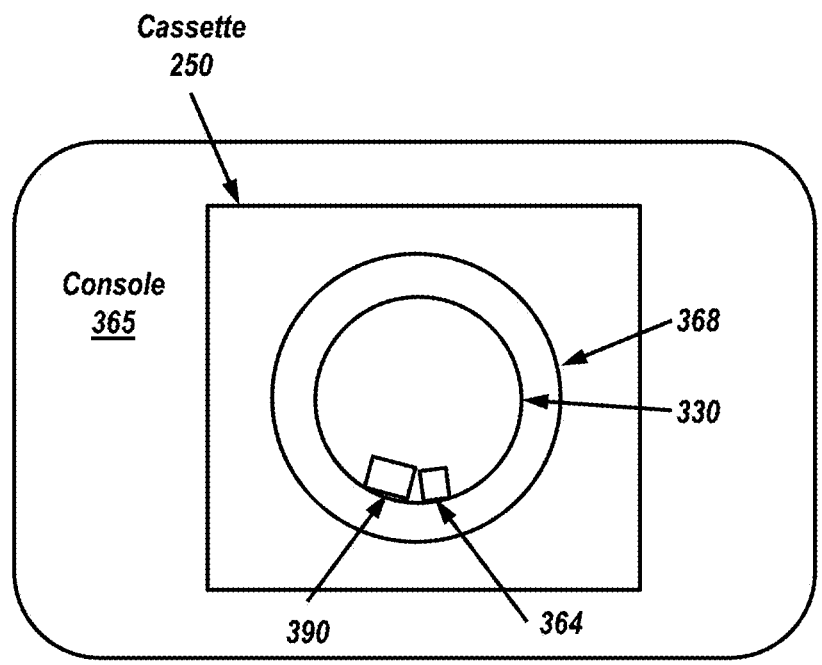
FIG. 7A shows another view of the cassette tracking system of FIG. 7, where the protrusion from the wheel meets the latch of the rotating track.

FIG. 7A shows a combined view of cassette 250 inserted in console 365 of a cassette system (e.g., 200). Here, the example shows a new cassette with wheel 330 having protrusion 390 positioned at a "start" position next to structure 364 of console track 368. As explained above, after each user, wheel 330 may rotate, causing protrusion 390 to rotate in a clockwise direction until it is blocked from the other side of structure 364, indicating that the cassette 250 may no longer be used. In other illustrative embodiments, the usage tracking system may include two gears, one in the console 365 and one in the cassette 250, that interact with each other to rotate or advance a wheel with each use of the cassette 250 until the wheel is prevented from any further rotation due to the maximum number of uses being reached. Other similar embodiments of a tracking mechanism may be within the scope of the present disclosure.

In another embodiment, track 368 may have a predefined shaped, e.g., a crescent, c-shape, u-shape, or incomplete circle or square, that permits protrusion 390 to following from a first point indicating the first use to a second point indicating the last use, wherein there is a defined distance between the first point and the second point permitting a defined number of uses of cassette 250 by permitting movement of protrusion 390 between the first point and the second point. The distance between the first point and the second point can be defined to allow varying number of interval distances corresponding to the number of permitted uses per cassette. As wheel 330 rotates in cassette 250, protrusion 390 rotates and moves along track 368 and will continue to function until it reaches the second point of track 368.

Figure 7B:
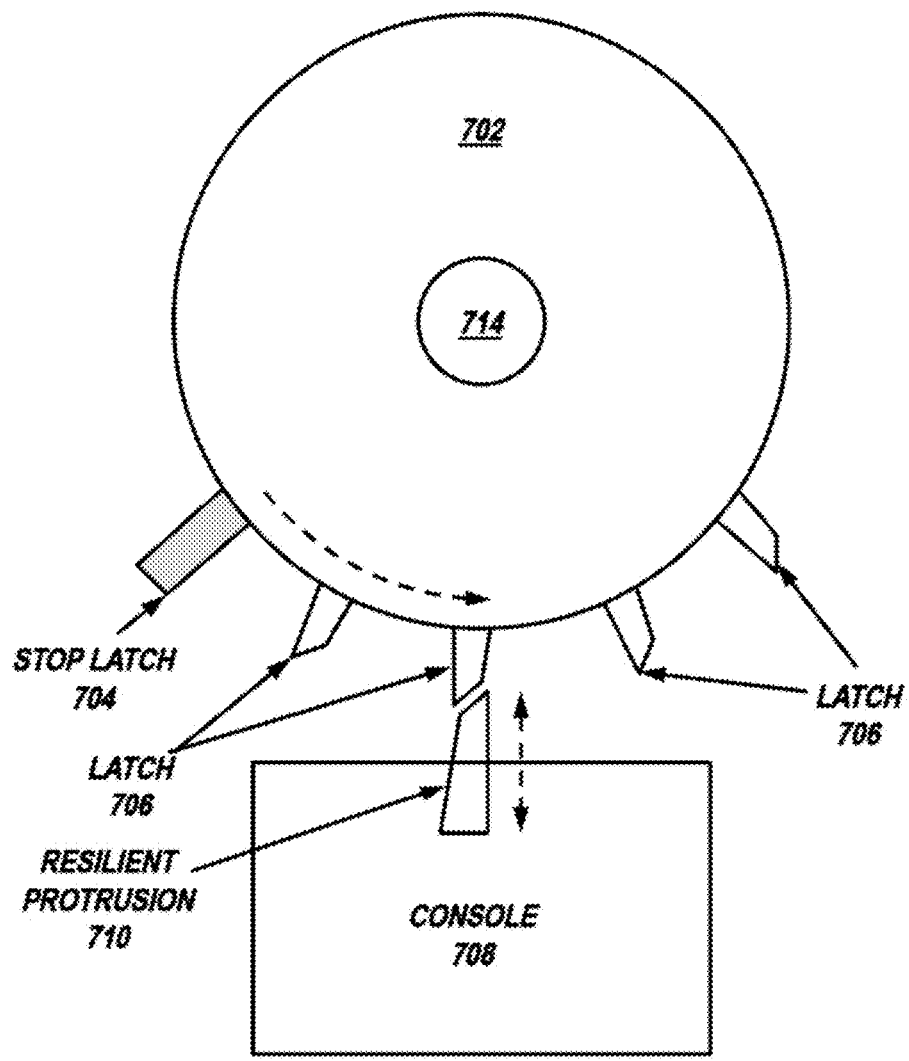
FIG. 7B illustrates another exemplary cassette tracking system for determining cassette usage, the cassette tracking system including a rotating track with a latch that contacts a resilient protrusion in the console for tracking and/or preventing cassette usage beyond a predetermined limit.

FIG. 7B shows another illustrative embodiment including wheel 702 configured to rotate axially around shaft 714 in the direction of the dotted arrow shown in FIG. 7B. In this example, wheel 702 houses a plurality of latches 706 that extend along the circumference of wheel 702, where the latches 706 are statically fixed. In one embodiment, each of the latches 706 may be shaped to facilitate or assist passage across resilient protrusion 710. In the example of FIG. 7B, the latches 706 and resilient protrusion 710 are configured with an angled face that may be angled in a complementary manner to provide reduced surface resistance as each latch (706) passes across resilient protrusion 710. It should be understood by those skilled in the art that any suitable configuration (e.g., multi-angled, rounded, etc.) may be used for latch 706 and resilient protrusion 710 faces to achieve this effect.

As each latch 706 passes across resilient protrusion 710 during rotation, a portion or face of latch 706 comes in contact with resilient protrusion 710, which forces resilient protrusion 710 to retract to allow latch 706 to pass across. Once each latch 706 passes, the resilient protrusion 710 may spring back to accept the next oncoming latch 706. The retraction and spring-back is illustrated as the dotted arrow shown in FIG. 7B. In the example of FIG. 7B, the resilient protrusion 710 is shown as a part of console 708. However, it should be appreciated by those skilled in the art that resilient portion 710 may be configured in any suitable area of a cassette system (e.g., 200), and may also be independently mounted.

As explained elsewhere herein, each latch 706 may be configured to represent a single cassette usage. After each use, wheel 702 may be mechanically and/or electromechanically advanced rotationally until latch 706 passes across resilient protrusion 710, causing it to retract and spring back to its original position. Resilient protrusion 710 may be configured with a spring, coil, band, or any other suitable material known in the art to provide resilience to resilient protrusion 710. Under an illustrative embodiment, upon a final usage, stop latch 704 may be configured to have a shape that obstructs passage of stop latch 704 past resilient protrusion 710. In the example of FIG. 7B, stop latch 704 may be configured to extend further than any of latches 706, and/or be configured with a shape (e.g., square) that increases surface resistance and/or applies lateral force that exceeds the resilience of resilient protrusion 710, thus preventing the resilient protrusion 710 from retracting and not allowing the stop latch 704 to pass.

Figure 7C:
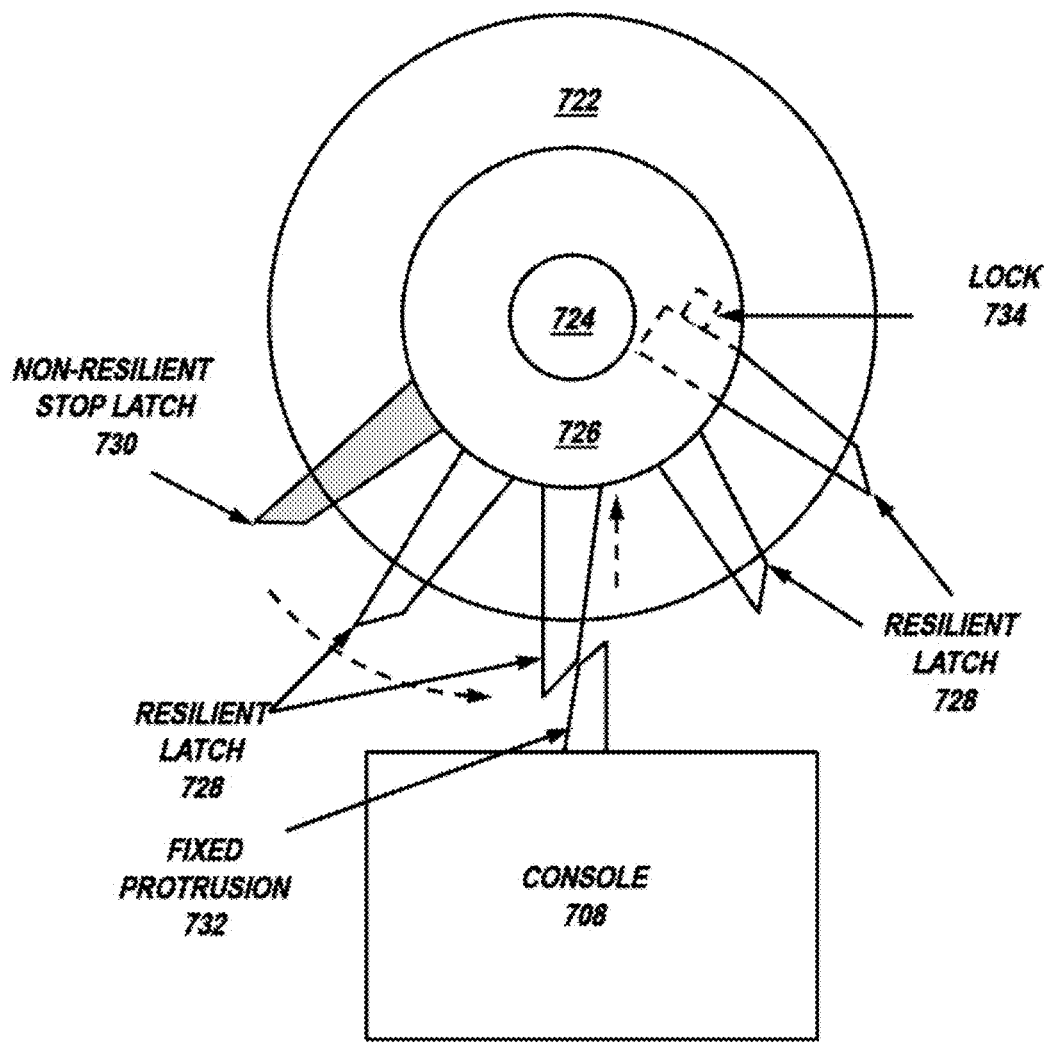
FIG. 7C illustrates another exemplary cassette tracking system for determining cassette usage, the cassette tracking system including a rotating track with a resilient latch that contacts a fixed protrusion in the console for tracking and/or preventing cassette usage beyond a predetermined limit.

FIG. 7C shows an illustrative embodiment that is similar to that of FIG. 7B, except that, instead of having fixed latches and a resilient protrusion, each of the latches are resilient, and the protrusion is fixed. In this example, wheel 722 includes a resilient latch housing 726 that holds a plurality of resilient latches 728, and rotates axially around shaft 724. In one illustrative embodiment, as each resilient latch 728 rotates and comes in contact with fixed protrusion 732, the force of the contact causes resilient latch 728 to retract to allow latch 728 to pass. In one illustrative embodiment, resilient latch 728 may spring back after passing. In another illustrative embodiment, resilient latch 728 may include a lock 734 that locks latch 728 into a retracted position within housing 724. Such a configuration may be advantageous to allow visual inspection to determine the number of uses, and/or the number of uses remaining. While not shown in FIG. 7C, an individual or universal release mechanism may be provided within latch housing 726 to release locked resilient latches 728 back to their extended (non-compressed) positions. This configuration would be advantageous in circumstances where a user would re-use wheels 722 after all of the uses have been registered for a particular cassette system.

Similar to the embodiment of FIG. 7B, each resilient latch 728 may be configured to represent a single cassette usage. After each use, wheel 722 may be mechanically and/or electromechanically advanced rotationally until each resilient latch 728 passes across fixed protrusion 732, causing each to retract. Resilient latches 728 may each be configured with a spring, coil, band, or any other suitable material known in the art to provide resilience to each latch. Under an illustrative embodiment, upon a final usage, a non-resilient stop-latch 730 may be configured as a fixed latch that stops further rotation of wheel 722 when coming in contact with protrusion 732 to indicate a final use for a cassette system. In an illustrative embodiment, stop latch 730 may also be configured to extend further than resilient latches 728 and/or have a shape that increases surface resistance to that obstruct passage of stop latch 730 past protrusion 732.

Figure 7D:
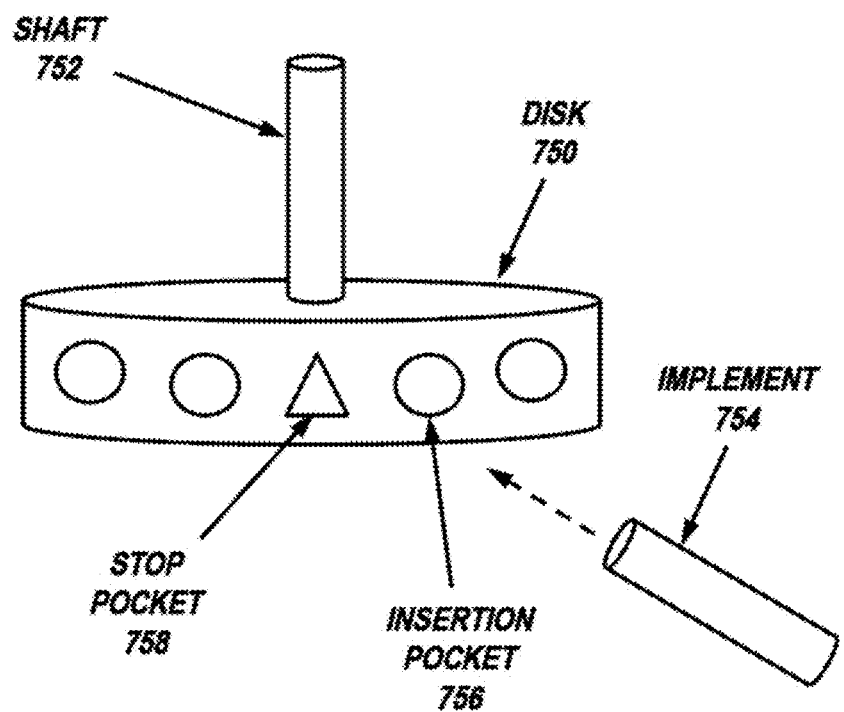
FIG. 7D illustrates another exemplary cassette tracking system for determining cassette usage, the cassette tracking system including a rotating disc with insertion pockets configured to mate with an implement for tracking and/or preventing cassette usage beyond a predetermined limit.

FIG. 7D shows a further embodiment where a disk 750 inside the cassette is coupled to shaft 752 inside the console to allow disk 750 to rotate mechanically and/or electromechanically after each cassette system usage. In this example, disk 750 is configured with a plurality of insertion pockets 756 shaped and extending radially from the circumference of disk 750 to receive similarly-shaped implement 754. By utilizing sensors (e.g., sensor 304), the system can determine when the implement is extended into each insertion pocket 756. In an illustrative embodiment, insertion pockets 756 may be configured with rounded or beveled edges to allow the implement 754 to slide with reduced friction/resistance from one insertion pocket to the next.

Similar to the embodiments of FIG. 7B and 7C, each insertion pocket 756 may be configured to represent a single cassette usage. After each use, disk 750 may be mechanically and/or electromechanically advanced rotationally such that implement 754 inserts and releases from each successive insertion pocket 756. In an illustrative embodiment, implement 754 may be configured with a spring, coil, band, etc. to ensure a more secure insertion in to each insertion pocket 756. Upon a final usage, a stop pocket 758, having a different shape (or not having a pocket in the stop position) from insertion pockets (756) and/or configured to obstruct implement 754, prevents implement 754 from fully inserting, indicating a final use for a cassette system and preventing further use of the cassette.

It should be understood by those skilled in the art that the present disclosure contemplates a plurality of modifications to the illustrative embodiments provided herein. For example, stop pocket 758 may be configured to have the same shape as insertion pockets 756, but having a different depth. For example, stop pocket 758 may be configured to have a deeper depth, which, in effect, would prevent the implement 754 from proceeding further. In another example, the latches, protrusions, pockets and implements may be manufactured from (or coated with) an electrically conductive material. Utilizing sensor circuitry (e.g., 304-305), a cassette system may determine a use from each time contact is made. In one example, latches (706, 728) may be configured to rotate and make contact with a respective protrusion (710, 732). The cassette system may be configured to allow further operation only when such electrical contact is detected. By configuring stop latches (704, 730) to be made from non-conductive material, a cassette system would stop operation, since no electrical contact would be detected. Similarly, insertion pockets (756) could include electrical contacts to detect coupling with a suitably conductive implement 754. A stop pocket (758) may be configured without an electric contact to indicate a final use. Of course, one skilled in the art would recognize that a reverse configuration is contemplated as well, i.e., allowing the cassette system to operate when no electrical contact is detected, and stopping use when contact is detected (e.g., providing an electrical contact only in the stop latch/pocket).

Figure 8:
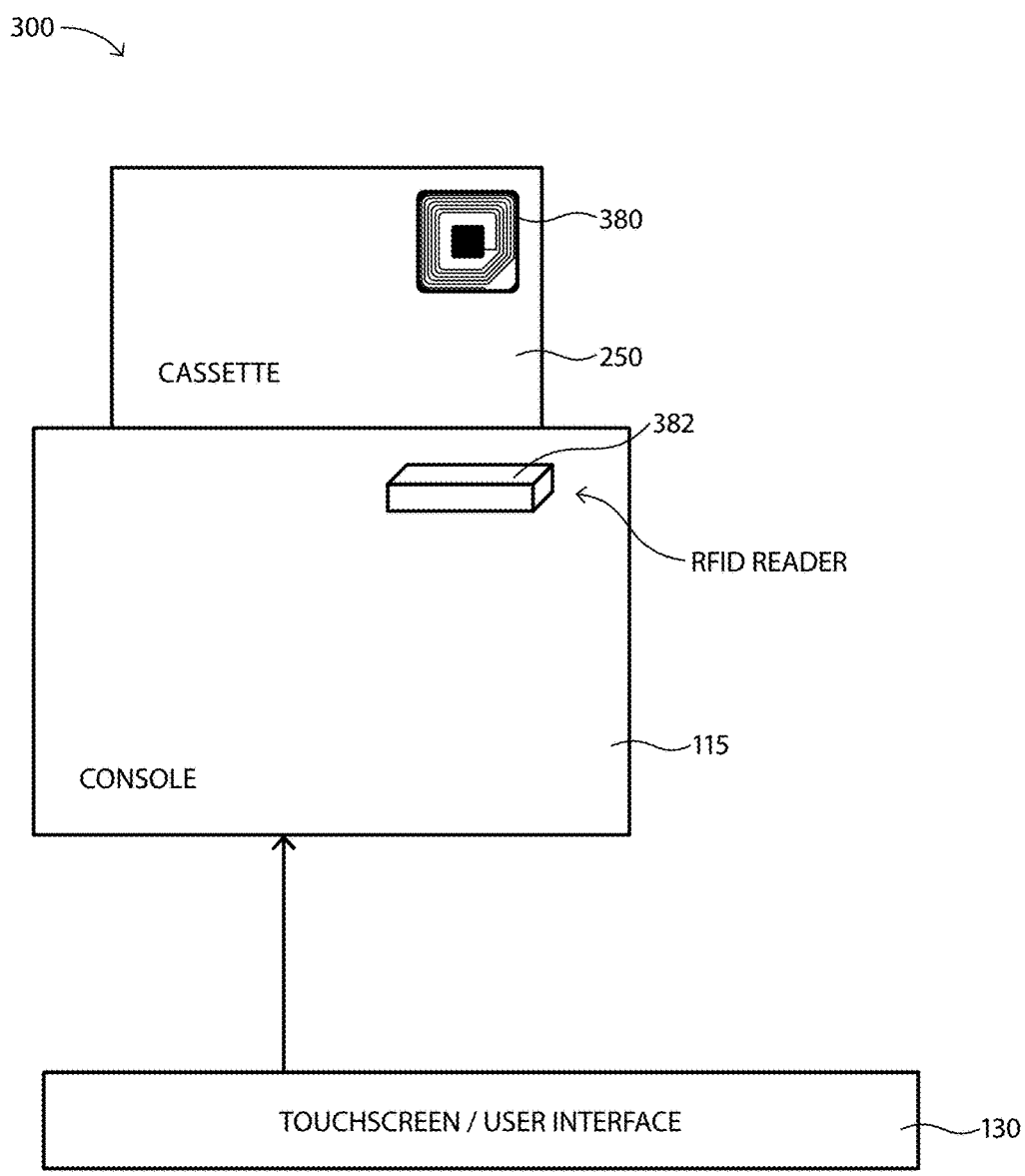
FIG. 8 is a functional block diagram of an exemplary cassette system under another embodiment, the cassette system being connected to a console, the cassette system including an RFID chip that is readable by the console.

Turning to FIG. 8, another exemplary embodiment of a usage tracking system 300 is provided including a passive RFID chip 380 that is coupled to the cassette. The RFID chip 380 can indicate and track the number of uses of a particular cassette, and relay that information to an RFID reader 382 located, for example, on the console 115. The RFID chip 380 may also identify the maximum number of uses for a cassette. In such embodiments, multiple phacoemulsification systems in a network may be linked via WiFi or some other connections so that if the same cassette is used on one machine and transferred to another it can be detected and the use counted. In such embodiments, there may be global network control of cassette usage as well.

Figure 9:
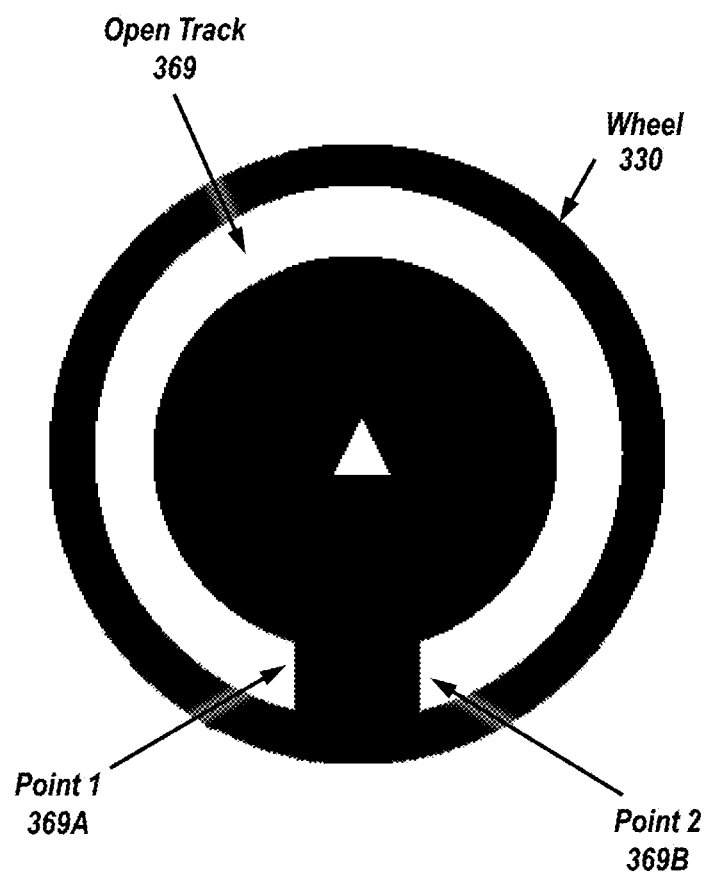
FIG. 9 shows another illustrative embodiment of a wheel suitable for use in a cassette tracking system, where the wheel includes an open track configured to receive a protrusion or structure, and wherein the track has a first starting point and a second ending point that prevents further advancement by the protrusion.

FIG. 9 shows an illustrative embodiment of a wheel arrangement, suitable for use in the embodiments of FIGS. 7-7A, or other embodiments of the present disclosure. In this example, wheel 330 includes an open track 369 that may travel along a circumpherential area of wheel 330 as shown in the figure. The open track 369 may be configured to receive a protrusion or structure (e.g., 364) such that the protrusion would be positioned at point 1 (369A) after initial insertion of a cassette (e.g., 250) into a console (e.g., 365). As the wheel 330 is rotated, the inserted structure would follow the path defined by open track 369 until it reaches point 2 (369B), at which point the structure would be blocked from further rotation (similar to the blocking provided by protrusion 390 and structure 364 configuration described above in connection with FIGS. 7-7A). It should be understood that wheel 330 of FIG. 9 may be arranged from either a cassette 250 side or a console 365 side. Thus, if cassette 250 was configured with wheel 330 of FIG. 9, the structure 364 would be configured to be insertably coupled to open track 369. Conversely, if console 365 was configured with wheel 330 of FIG. 9, the protrusion 390 would be configured to be insertably coupled to open track 369.

Those of ordinary skill in the art may recognize that many modifications and variations of the herein disclosed systems and methods may be implemented without departing from the spirit or scope of the invention. Thus, it is intended that the present invention covers such modifications and variations provided they come within the scope the appended claims and their equivalents.

What is claimed is:

1. A reusable cassette sensing apparatus, configured to be part of a surgical device, comprising:
a film configured to indicate a maximum number of uses of the surgical device;
a tracking system comprising an implement, at least one sensor and a processor, wherein the implement is configured to irreversibly modify the film, and wherein the at least one sensor is configured to sense the maximum number of uses from the film, and, prior to a use of the surgical device, the processor is configured to determine if the maximum number of uses has been reached based at least on a number of irreversible modifications of the film, by the implement.

2. The reusable cassette sensing apparatus of claim 1, wherein the processor is configured to provide a signal indicating the maximum number of uses has been reached.

3. The reusable cassette sensing apparatus of claim 2, wherein the signal comprises at least one of a warning signal, a disable signal and an eject signal.

4. The reusable cassette sensing apparatus of claim 1, wherein the at least one sensor is configured to sense the maximum number of uses from the film via at least one of optical and electrical scanning of the film.

5. The reusable cassette sensing apparatus of claim 1, wherein the at least one sensor is configured to sense the maximum number of uses from the film via a film identifier affixed to the film.

6. The reusable cassette sensing apparatus of claim 5, wherein the film identifier comprises one of a bar code, a QR code and a RFID tag.

7. The reusable cassette sensing apparatus of claim 1, wherein the implement comprises one of a punch, cutter, ink ejection, and light emitter.

8. A method for tracking usage of a reusable cassette, configured to be part of a surgical device, comprising:
sensing, prior to use of the surgical device, a maximum number of uses from a film configured to indicate a maximum number of uses of the reusable cassette;
provided that the maximum number of uses has not been reached, activating an implement to irreversibly modify the film; and
based at least in part on the number of irreversible modifications of the film by the implement, determining a remaining number of usage for the reusable cassette.

9. The method of claim 8, further comprising the step of providing a signal indicating the maximum number of uses has been reached based on the sensing.

10. The method of claim 9, wherein the signal comprises at least one of a warning signal, a disable signal and an eject signal.

11. The method of claim 8, wherein the sensing composes sensing the maximum number of uses from the film via at least one of optical scanning and electrical sensing of the film.

12. The method of claim 8, wherein the sensing the maximum number of uses from the film comprises sensing via a film identifier affixed to the film.

13. The method of claim 12, wherein the film identifier comprises one of a barcode, a QR code and a RFID tag.

14. The method of claim 8, wherein the implement comprises one of a punch, cutter, ink ejection, and light emitter.

\* \* \* \* \*